US012611093B2

(12) United States Patent
Craig et al.

(10) Patent No.: US 12,611,093 B2
(45) Date of Patent: Apr. 28, 2026

(54) UTILIZATION OF MULTIPLE IMAGERS AND COMPUTATIONAL PHOTOGRAPHY IN ENDOSCOPY

(71) Applicant: ConvergAscent LLC, Minneapolis, MN (US)

(72) Inventors: Brian H. Craig, Minneapolis, MN (US); Dwight Meglan, Westwood, MA (US)

(73) Assignee: ELEMENTS ENDOSCOPY, INC., Minneapolis, MN (US)

( * ) Notice: Subject to any disclaimer, the term of this patent is extended or adjusted under 35 U.S.C. 154(b) by 449 days.

(21) Appl. No.: 17/775,609

(22) PCT Filed: Nov. 20, 2020

(86) PCT No.: PCT/US2020/061424
§ 371 (c)(1),
(2) Date: May 10, 2022

(87) PCT Pub. No.: WO2021/102217
PCT Pub. Date: May 27, 2021

(65) Prior Publication Data
US 2022/0395166 A1 Dec. 15, 2022

Related U.S. Application Data

(60) Provisional application No. 62/939,261, filed on Nov. 22, 2019.

(51) Int. Cl.
*A61B 1/05* (2006.01)
*A61B 1/06* (2006.01)
*H04N 7/18* (2006.01)

(52) U.S. Cl.
CPC .................. *A61B 1/05* (2013.01); *A61B 1/06* (2013.01); *H04N 7/183* (2013.01); *A61B 1/0684* (2013.01)

(58) Field of Classification Search
CPC ........... A61B 1/05; A61B 1/06; A61B 1/0684; H04N 7/183
See application file for complete search history.

(56) References Cited

U.S. PATENT DOCUMENTS 4,880,011 A * 11/1989 Imade .................. A61B 8/4461
600/101
6,315,712 B1 11/2001 Rovegno
(Continued)

FOREIGN PATENT DOCUMENTS

CN 109561810 A 4/2019
WO 2013025530 A1 2/2013

OTHER PUBLICATIONS

OV6948 product brief (Year: 2019).*
Omnivision OV6948 product brief (Year: 2019).*
Omnivision OV6948 product brief {Current Guinness World record title issued to OmniVision Technologies, Inc.: Smallest Commercially Available Image Sensor. The smallest commercially available image sensor is the OV6948, measuring 0.575 mm×0.575 mm×0.232 mm, made by OmniVision Technologies,Inc. USA (Year: 2019).*
(Continued)

*Primary Examiner* — Michael J Carey
*Assistant Examiner* — Megan Elizabeth Monahan
(74) *Attorney, Agent, or Firm* — MEDLER FERRO WOODHOUSE & MILLS PLLC

(57) ABSTRACT

An endoscopy system having a low-profile multi-imager endoscope. The system is capable of using computational photography to provide enhanced output images using techniques such as super-resolution, foveation, magnification, and two-dimensional to three-dimensional conversion. The enhanced output images can improve clinical decision making and patient treatment. Signals from multiple imagers may be used to affect/adjust handing characteristics of the endoscope or direct semi-robotic guidance thereof.

13 Claims, 7 Drawing Sheets

(56) References Cited

U.S. PATENT DOCUMENTS

| | | | |
|---|---|---|---|
| 6,652,452 B1 | 11/2003 | Seifert et al. | |
| 9,129,422 B2 | 9/2015 | Mountney et al. | |
| 9,931,023 B2 | 4/2018 | Shahinian et al. | |
| 10,064,545 B2 | 9/2018 | Hua et al. | |
| 2005/0018042 A1 | 1/2005 | Rovegno | |
| 2005/0096501 A1* | 5/2005 | Stelzer | A61B 1/00098 |
| | | | 600/101 |
| 2013/0096378 A1* | 4/2013 | Alexander | A61B 1/00114 |
| | | | 606/191 |
| 2015/0036014 A1 | 2/2015 | Lelescu et al. | |
| 2017/0164821 A1* | 6/2017 | Levy | A61B 1/00188 |
| 2017/0280988 A1* | 10/2017 | Barbato | A61B 1/317 |
| 2019/0004308 A1* | 1/2019 | Iwama | A61B 1/00052 |
| 2020/0054203 A1* | 2/2020 | Shreim | A61B 5/0075 |

OTHER PUBLICATIONS

Raskar, R. (2007). Less Is More: Coded Computational Photography. In: Yagi, Y., Kang, S.B., Kweon, I.S., Zha, H. (eds) Computer Vision—ACCV 2007. ACCV 2007. Lecture Notes in Computer Science, vol. 4843. Springer, Berlin, Heidelberg. https://doi.org/10.1007/978-3-540-76386-4_1 (Year: 2007).*

Extended European Search Report issued Oct. 30, 2023 in EP Appl. No. 20 889 110.1.

International Search Report issued Feb. 22, 2021 in Int'l Appl. No. PCT/US2020/061424.

* cited by examiner

UTILIZATION OF MULTIPLE IMAGERS AND COMPUTATIONAL PHOTOGRAPHY IN ENDOSCOPY

TECHNICAL FIELD

The present disclosure relates generally to endoscopes and associated systems and methods.

BACKGROUND

An endoscope is an illuminated optical, typically slender and tubular instrument used to look deep into the body. A flexible endoscope has a flexible insertion tube with a distal segment that can be controllably deflected by tensioning control cables to navigate the sometimes-tortuous pathways through the body. Besides having a digital imager and LED light source at the distal end, many current endoscopes have an insertion tube large enough to provide an open working channel therethrough for passing medical instruments. An endoscope may be designed for use in particular diagnostic or therapeutic endoscopy procedures, and is named accordingly, for example gastrointestinal endoscope, duodenoscope, bronchoscope, cystoscope, ureteroscope, or hysteroscope.

DETAILED DESCRIPTION

The present disclosure relates generally to endoscopes and associated systems and methods. Specific details of several embodiments of the present technology are described herein with reference to FIGS. 1-16. Although many of the embodiments are described with respect to endoscope devices, systems, and methods, other embodiments in addition to those described herein are within the scope of the present technology. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of an endoscope). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

Figures 1, 2:
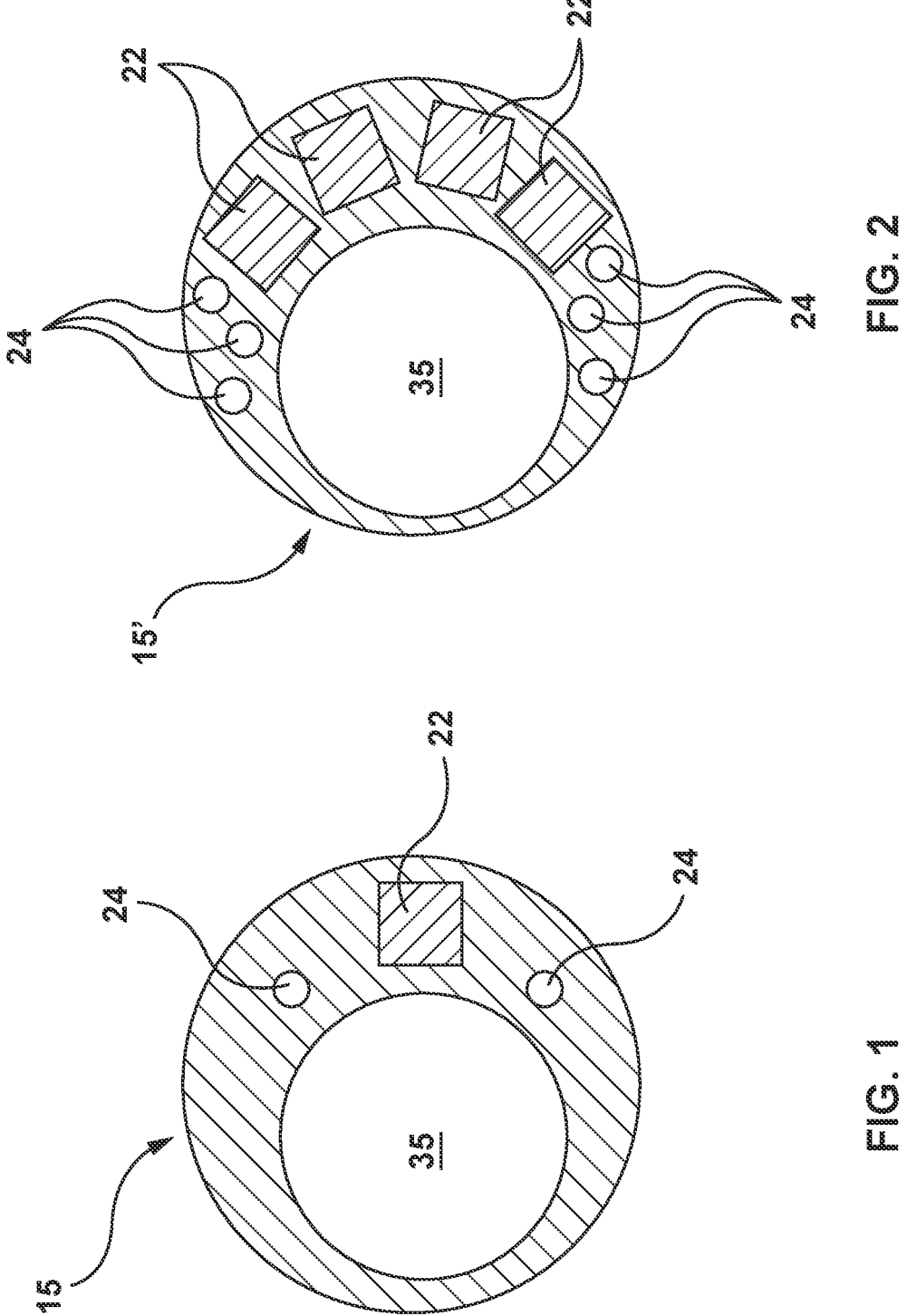
FIG. 1 is a distal end view of a low-profile single-imager endoscope in accordance with an embodiment of the present technology.
FIG. 2 is a view of a distal end of a multiple-imager endoscope in accordance with an embodiment of the present technology.

It is advantageous for an endoscope to have a relatively small cross-sectional size to facilitate advancement through the patient anatomy. FIG. 1 shows a low-profile endoscope 15 in accordance with the present technology wherein the image sensor 22 is an ultra-small color CMOS analog 40K pixel array OV6948 sold by Omnivision Technologies, Inc., Santa Clara, CA, U.S.A., measuring only 0.575 mm×0.575 mm. In combination with one working channel 35 having a 2.1 mm diameter and two light sources 24 each measuring 0.2 mm, the resulting insertion tube 20 can have a circular diameter as small as 3.25 mm. While such an endoscope represents a technical advance in down-sizing, the image resolution is compromised at 200×200 pixels as compared to 400×400 pixel medical image sensors commonly found in current endoscopes.

The endoscope 15' shown in FIG. 2 maintains the advantageous low profile and the same 2.1 mm working channel of the embodiment of FIG. 1, but the pixel count of the device is increased by fitting additional OV6948 imagers into the annular wall space at the distal end of the insertion tube 20. As illustrated, four 200×200 pixel imagers are mounted facing distally in the endoscope distal tip 23 resulting in a total pixel count of 160K, which is comparable to the pixel count in a typical endoscope equipped with a 400×400 pixel sensor. However, because the four individual 200×200 pixel image sensors are arranged in an array spanning nearly the full diameter of the endoscope tip, the ultimate output image resolution will greatly exceed that achievable with a single 400×400 pixel sensor, as described in further detail below. Thus, providing two or more ultra-small medical image sensors in an endoscope can result in a reduced profile device without degrading final output image resolution or reducing working channel size. The image sensors may be close-packed or spaced apart in a symmetrical or non-symmetrical arrangement to fit into space available on the endoscope distal tip. As a further modification of the embodiment shown in FIG. 1, additional, e.g. four, 0.2 mm light sources 24 are also fitted at the distal end of the device shown in FIG. 2. The light sources 24 can be one or more distally-mounted light-emitting diodes (LEDs) or fiber optic light guides also called light pipes, or combinations thereof. One of ordinary skill in the art of endoscopes will understand that other embodiments are possible such as smaller diameter endoscopes featuring only three or two ultra-small image sensors at the distal tip, and/or a reduced diameter working channel. Additionally, larger diameter endoscopes can comprise more than four ultra-small image sensors at the distal tip and offer correspondingly higher output image resolution.

As shown in FIGS. 3-6, an endoscope system 10 includes a flexible endoscope 15, a computer 16, and a monitor 17. Monitor 17 is located separately from or extrinsic to endoscope 15 and communication therebetween may be wireless (e.g. WLAN, WPAN radio networks) or via an electrical cable or data port 18 as indicated by broken lines in FIG. 3. Endoscope 15 includes an elongate assembly having a distal region configured for insertion into a living body, the entire assembly referred to herein as a flexible elongate insertion tube 20.

An image sensor or optical module 22 is disposed at distal end 21 of insertion tube 20 and is adapted to receive images of an interior of a hollow organ or other targeted cavity of a living body. Optical module 22 can be selected from various configurations, none of which is shown. In a first configuration, optical module 22 comprises an outer casing, a lens or lens assembly, a PCB containing a camera chip and a connector that may be directly mounted on the PCB or attached to the PCB via a flexible electrical cable. An illumination source 24 may be separate from the optical module and integrated elsewhere into the endoscope body, as shown in FIGS. 1 and 2. In a second configuration, optical module 22 comprises an outer casing, a lens or lens assembly, an LED lighting system, a PCB containing a camera chip and a connector that may be directly mounted on the PCB or attached to the PCB via a flexible electrical cable. Alternatively, more than one optical module 22 may be mounted at distal end 21 of insertion tube 20, as shown in the embodiment of FIG. 2.

Figures 4, 5, 6:
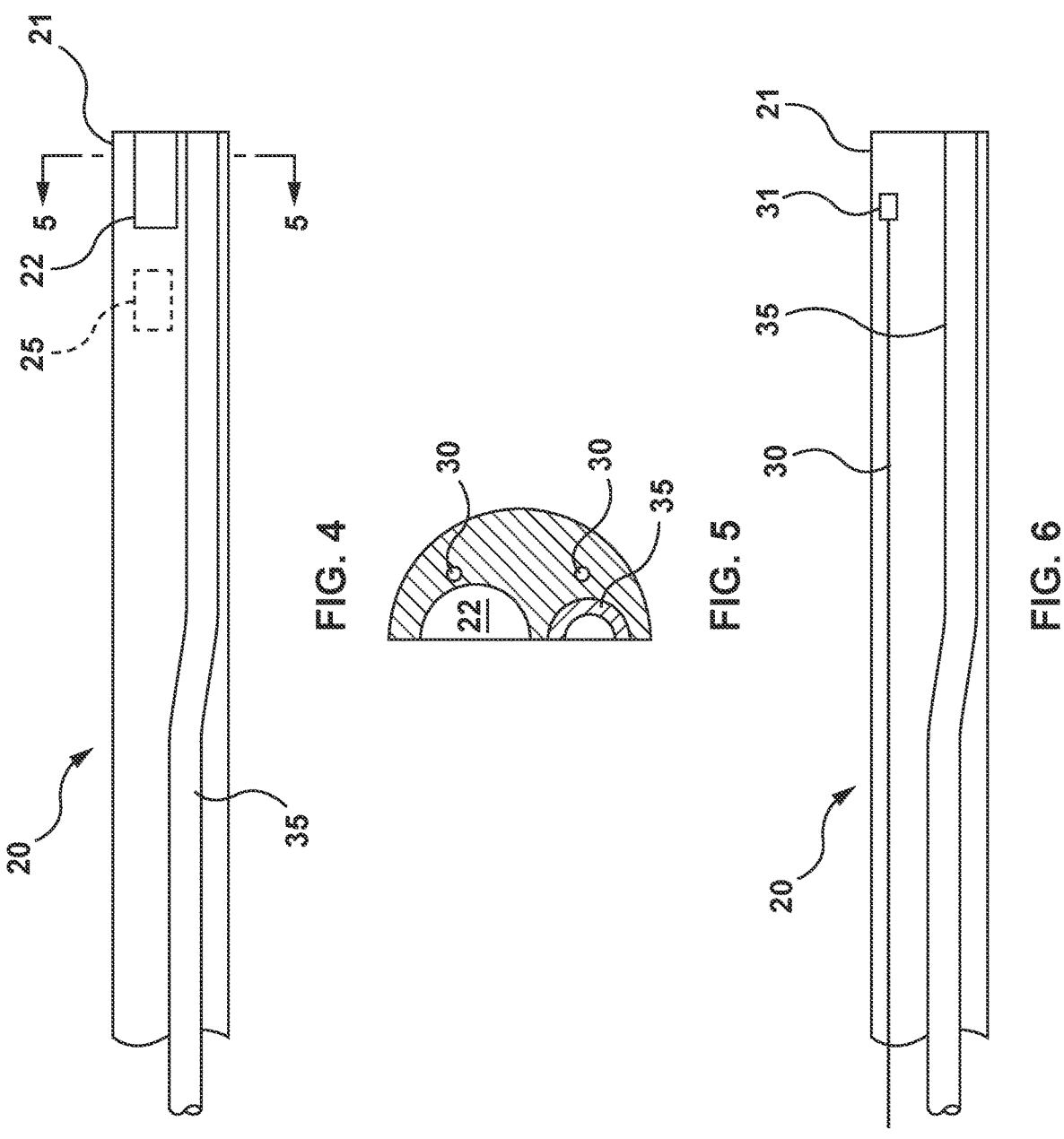
FIG. 4 shows a longitudinal cross-sectional and partially schematic view of a distal portion of an endoscope in accordance with embodiments of the present technology.
FIG. 5 is a transverse cross-sectional view of the distal portion of the endoscope of FIG. 4, taken along line 5-5.
FIG. 6 shows another longitudinal cross-sectional and partially schematic view of a distal portion of an endoscope in accordance with embodiments of the present technology.
Figures 7, 8, 9:
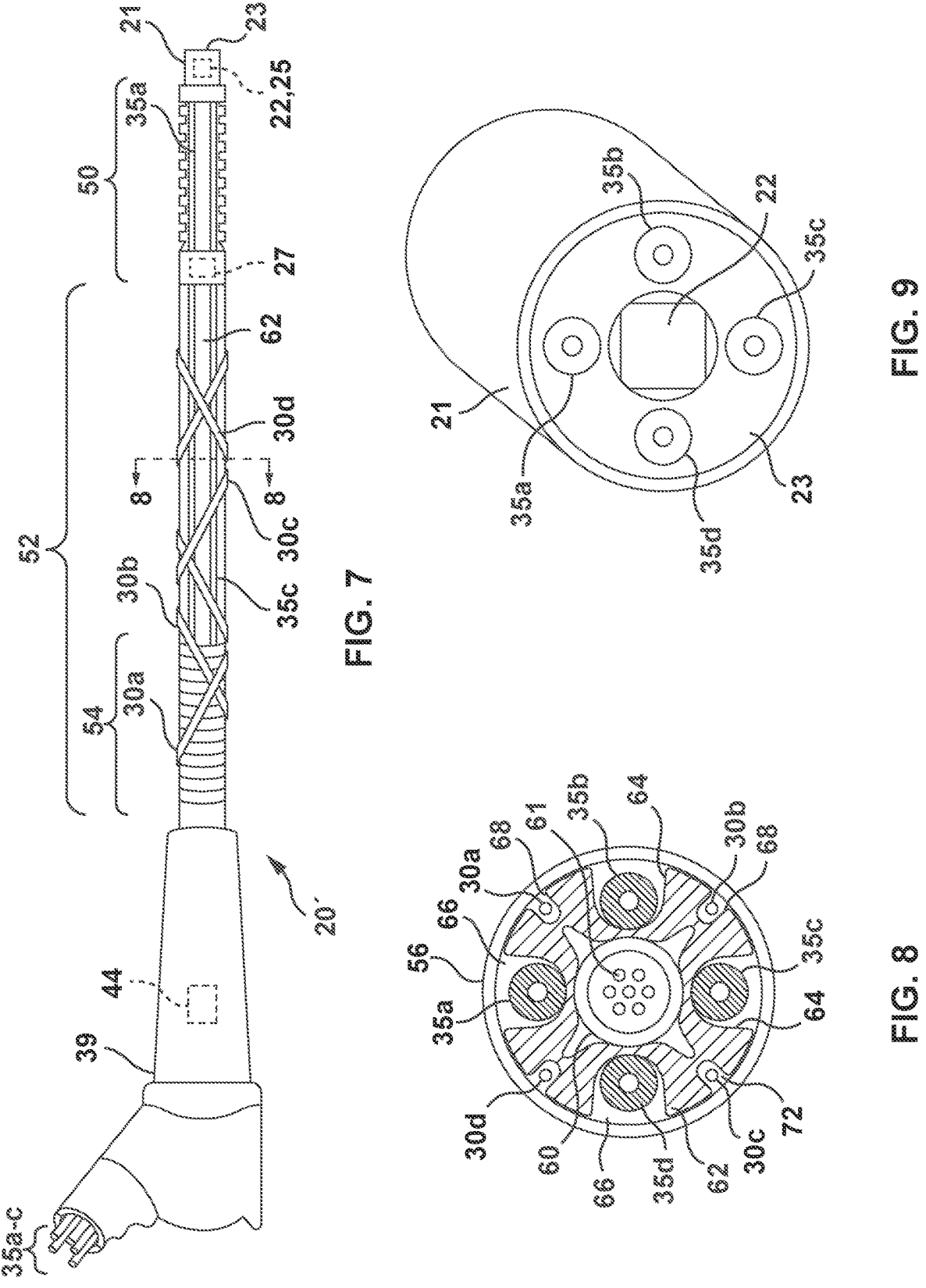
FIG. 7 is a side view of an insertion tube in accordance with another embodiment of the present technology. The outer sheath is omitted for clarity.
FIG. 8 is a transverse cross-sectional view of the insertion tube of FIG. 7, taken along line 8-8.
FIG. 9 is an isometric view of the distal end of the insertion tube of FIG. 7.
Figure 10:
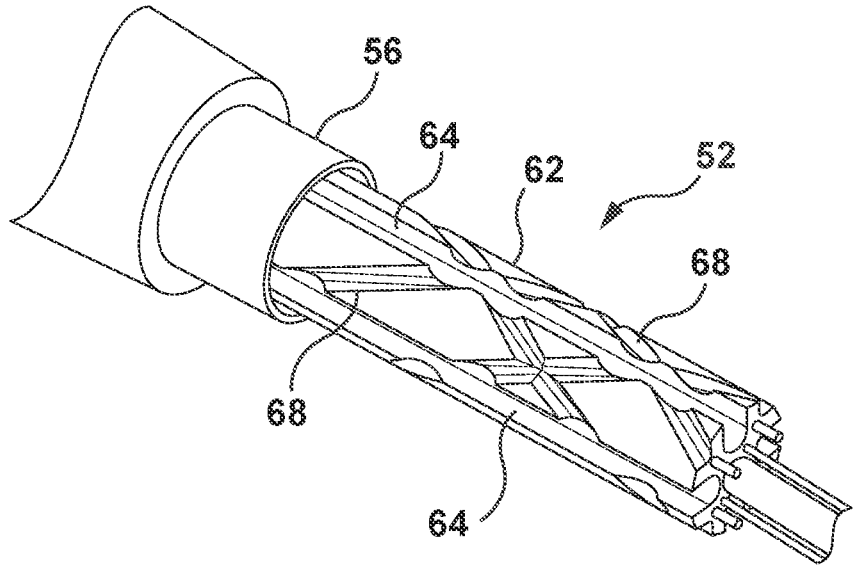
FIG. 10 is a cutaway drawing of the intermediate segment of the insertion tube of FIG. 7. Tubular working channels and control cables are omitted for clarity.

Insertion tube 20 also includes one or more distal inertial measurement units (IMUs) 25 disposed at tube distal end 21. IMUs 25 may be incorporated into optical module 22 or mounted separately therefrom, as illustrated in FIG. 4. As shown in FIG. 7 and described below, an intermediate IMU 27 may also be disposed at the proximal end of distal segment 50. An inertial measurement unit is an electronic device that measures and reports an object's specific acceleration, angular rate, and magnetic field surrounding the object, using a combination of accelerometers, gyroscopes, and magnetometers. An IMU works by detecting linear acceleration, rotational rate, and heading reference. When applied to each axis, an IMU can provide pitch, roll, and yaw as well as linear movement. When incorporated into Inertial Navigation Systems, the raw IMU measurement data are utilized to calculate attitude, angular rates, linear velocity and position relative to a global reference frame. IMU data allows a computer to track an object's position, using a method known as dead reckoning or the process of calculating one's current position by using a previously determined position, or fix, and advancing that position based upon known or estimated speeds over elapsed time and course. IMU navigation can suffer accuracy limitations from accumulated error or drift. This error is expected to be reduced in the present technology by combining IMU data with image data generated by optical module 22 such that each subsequent image serves as both a new and a cumulative navigational reference. Associating each image frame or a sampling of image frames with a discrete distal IMU pose data point to create a discrete image pose datum is expected to allow navigation errors to be removed.

As shown in FIGS. 5 and 6, a plurality of control cables 30 extend proximally through insertion tube 20 from corresponding anchor points 31 at insertion tube distal end 21. As will be understood by a person of ordinary skill in the field of endoscopes, cables 30 may be tensioned singly or in various combinations to alter the shape and/or torsional or bending stiffness of insertion tube 20 to facilitate navigating the sometimes-tortuous pathways through the living body. Actuators for applying tension to cables 30 are described below.

Optionally, insertion tube 20 may include one or more working channel(s) 35 therethrough for delivery of fluids or tools as will be understood by a person of ordinary skill in the field of endoscopes.

FIGS. 7-11 illustrate another embodiment of an insertion tube 20' in accordance with the present technology. Insertion tube 20' includes, listed from distal end to proximal end, distal tip 21, distal segment 50, intermediate segment 52, strain relief segment 54, and proximal end connector 39. In a flexible endoscope embodiment, distal segment 50 may comprise a bendable active segment, and intermediate segment 52 may be a flexible segment. An outer sheath 56, shown in FIG. 8 but omitted from FIG. 7 for clarity, encloses all the components of insertion tube 20' located distal of connector 39 except for the distal end 23 of insertion tube 20', where optical module 22 is exposed as shown in FIG. 9.

Insertion tube 20' also includes elongate inner tube 60 with electrical wires 61 extending therethrough from connector 39 to, e.g. optical module 22 and IMUs 25, 27. Inner tube 60 is surrounded by elongate spine 62, which has one or more channel grooves 64 configured to receive one or more corresponding tubular working channels 35. See FIGS. 8 and 10. Channel grooves 64 extend longitudinally parallel to a centerline of spine 62 along flexible intermediate segment 52 and bendable active segment 50. In the exemplary embodiment, four working channels 35a-c extend from a side port in connector 39 to insertion tube distal end 23, and are confined to channel lumens 66 defined between channel grooves 64 of spine 62 and outer sheath 56.

Spine 62 has a plurality of cable grooves 68 configured to receive one or more corresponding cables 30. See FIGS. 8 and 10. Cable grooves 68 are helical along flexible intermediate segment 52 and extend longitudinally parallel to a centerline of spine 62 along bendable active segment 50. In the exemplary embodiment, four cables 30 extend from connector 39 to insertion tube distal tip 21, and are confined to cable lumens 72 defined between cable grooves 68 of spine 62 and outer sheath 56. A first and second pair of 180 degree opposed helical cable grooves 68 have reverse chirality or handedness such that the first and second pair of grooves 68 intersect or cross each other repeatedly along flexible intermediate segment 52. For example, cables 30a and 30c extend through respective cable lumens 72 of spine 62 to define a congruent double right-handed helix and cables 30b and 30d extend through respective cable lumens 72 of spine 62 to define a congruent double left-handed helix. Each pair of cable lumens 72, e.g. lumens carrying cables 30a and 30c, remains opposed 180 degrees along flexible intermediate segment 52 and bendable active segment 50 to balance tension forces and to define an orthogonal bending plane within active segment 50. At least at distal end 21, cables 30a and 30c are spaced 90 degrees from cables 30b and 30d to provide at least two orthogonal planes of bending in active segment 50. Since all cable grooves 72 are formed in spine 62 at the same radius from the center of spine 62, cables 30 may have sliding contact with each other where they intersect. Cables 30 extend proximally from corresponding anchor points 31 (see FIG. 4) to connector 39. As shown in FIG. 7, cables 30 are disposed around, i.e. outside of working channels 35. However, it is also an embodiment of the current technology for the spine grooves to be configured such that the working channels 35 are disposed outside of the cables 30.

Figure 11:
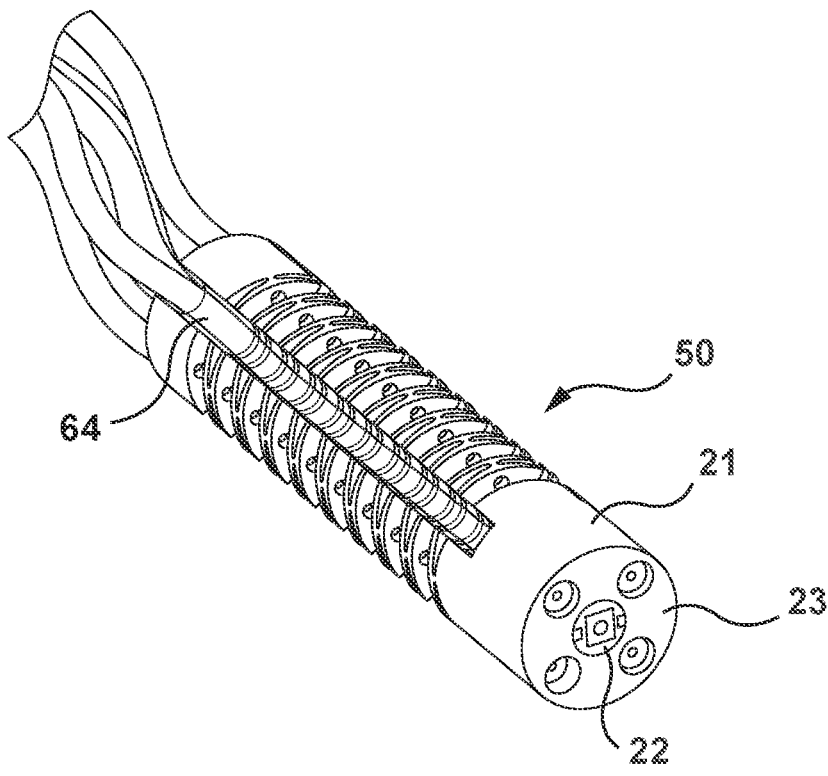
FIG. 11 is an isometric view of the distal end of the insertion tube of FIG. 7. The outer sheath, tubular working channels and control cables are omitted for clarity.

Bendable active segment 50 is configured to be sufficiently flexible to be deflectable in any direction in response to combinations of tensioning in control cables 30, as shown in FIG. 11. Flexible intermediate segment 52 may include intermediate IMU 27 disposed at the distal end thereof, and is less flexible than active segment 50. However, the torsional or bending stiffness of intermediate segment 52 can be controllably increased, for example, by simultaneously tensioning all cables 30. Thus, the torsional or bending stiffness of intermediate segment 52 can be altered regardless of the straight or deflected shape of active segment 50. Conversely, active segment 50 can be controllably deflected independently of the stiffness that may have been induced into intermediate segment 52. Optional strain relief segment 54 may be provided to further increase inherent stiffness and kink-resistance at the proximal end of insertion tube 20′. Strain relief segment 54 may comprise a spiral or helical coil of suitable metal or polymer, and may be disposed either inside or outside of cables 30, and either inside or outside of outer sheath 56. Outer sheath 56 encases all the components of insertion tube 20′ as described above to provide a sterility barrier and to provide mechanical properties that contribute significantly to the torsional and/or bending stiffness of insertion tube 20, 20′. For example, outer sheath 56 may provide 20-50% of the overall bending stiffness of fully assembled insertion tube 20.

Figure 3:
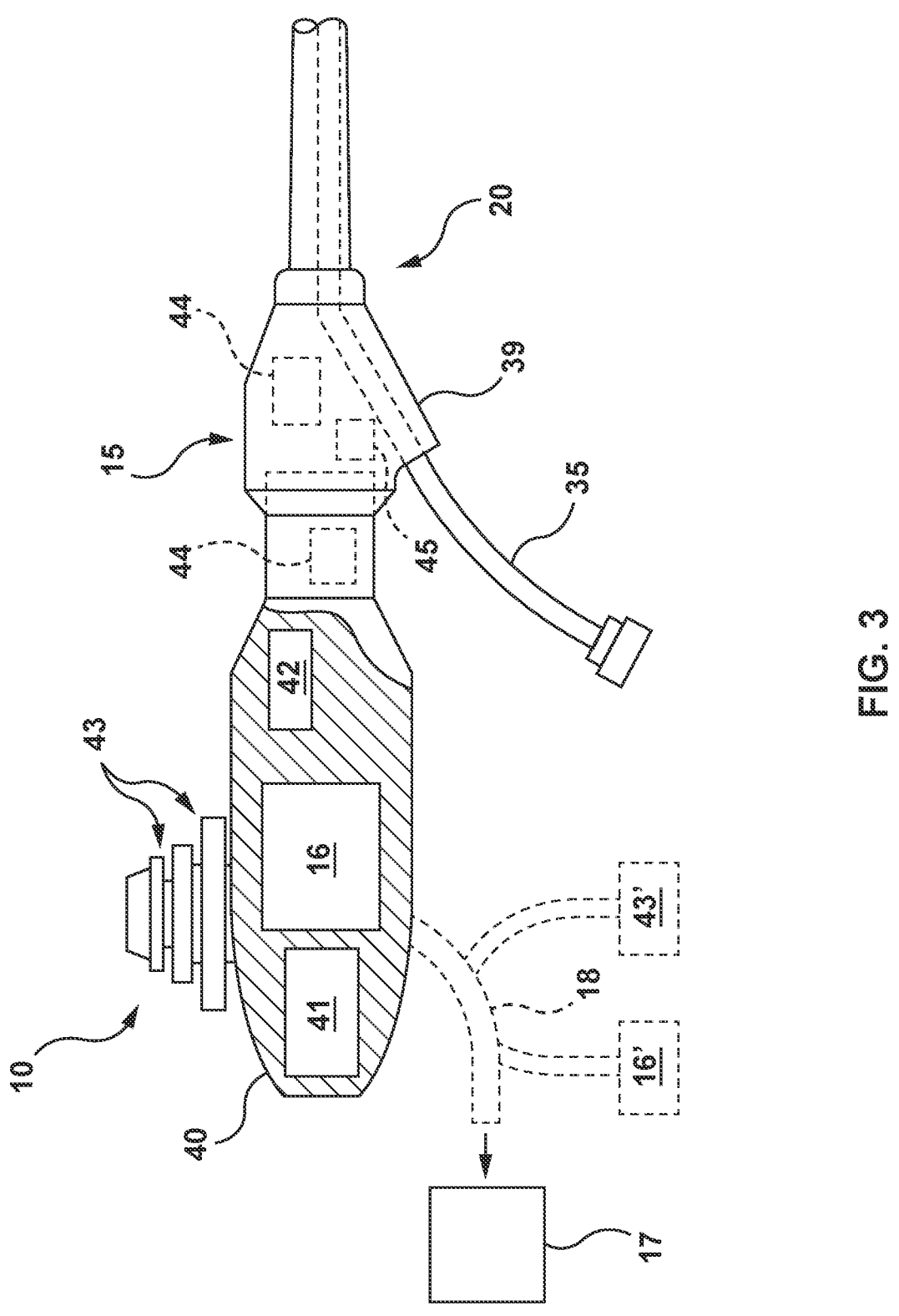
FIG. 3 is a partially schematic view of a proximal portion of an endoscope in accordance with embodiments of the present technology.

Flexible endoscope 15 includes a handle 40 connected to proximal end connector 39 of insertion tube 20. Handle 40 is also connectable to insertion tube 20′ or any other interchangeable members of an endoscope family having a common connector 39. One or more proximal IMUs 44 may be disposed in handle 40 and/or in connector 39 at the proximal end of insertion tube 20, as shown in FIGS. 3 and 7. A battery 41 may be mounted in handle 40 as shown. Optionally, electrical power may be provided to endoscope 15 via an electrical cable similar to cable 18. Alternatively, handle 40 is releasably connected to the proximal end of insertion tube 20. The releasable connection may be a quick-release type, such as a quarter-turn fastening or bayonet-type mount and may incorporate facilitated electrical connections for IMUs 25, 27, 44 and optical module 22 as well as facilitated mechanical connections between cables 30 and associated actuators 42.

Handle 40 includes a plurality of actuators 42, each actuator 42 being operatively associated with a corresponding cable extending proximally from insertion tube 20. Actuators 42 may be selected from various types of actuators including linear or rotary, electric (e.g. electro-mechanical), mechanical, hydraulic, pneumatic, twisted and coiled polymer (TCP) or supercoiled polymer (SCP), thermal or magnetic shape memory alloys. A single actuator 42 is shown in FIG. 3 for clarity of illustration, and a connection between actuator 42 and cable 30 is omitted for clarity and because the general concept of actuators and cables will be understood by a person of ordinary skill in the field of endoscopes.

One or more manually operable controllers, i.e. haptic input devices 43 are located on handle 40 for providing force feedback while inputting electronic commands for manipulating endoscope physical properties, i.e. for steering and/or adjusting the torsional and bending stiffness characteristics of insertion tube 20. Haptic input devices 43 may be any suitable type of programmable or pre-programmed kinesthetic or tactile communication devices such as magnetoresistive (MR) controls or motor controllers with feedback. Haptic devices 43 are illustrated as rotary controls that may simulate the steering wheels found on conventional endoscopes. Alternatively, other haptic input devices may be incorporated into handle 40 such as joysticks, touchpads, or keypads, etc. In another alternative embodiment, endoscope system 10 may include haptic input devices 43′ located separately from handle 40 as shown in FIG. 3. At the discretion of the clinician, haptic devices 43′ may be used to override any communications from haptic devices 43 on handle 40. In yet another alternative embodiment, input devices 43, 43′ are not haptic-type devices. Such non-haptic devices can input commands to computer 16 for manipulating endoscope physical properties in situations where force feedback is not required.

Computer 16 is illustrated as being physically mounted in handle 40. Alternatively, computer 16′ can be located separately from endoscope 15 on a conventional endoscopy tower 19 or "stack," and can communicate with endoscope 15 via cable or data port 18 as shown in FIG. 3. Computer 16 is configured for converting image data received from optical module 22 into two-dimensional images displayable on monitor 17. In alternative embodiments where endoscope 15 has more than one optical module 22, computer 16 is configured for converting image data received from the plurality of optical modules 22 into three-dimensional images displayable on monitor 17.

Computational photography can be applied to a multi-imager endoscope to create an output image having super-resolution, a resolution that is higher than merely summing the pixels of the plurality of sensors, i.e. four 200×200 pixel imagers equaling 160K pixels. Multiple-frame super-resolution merges data from low-resolution images into a more accurate higher-resolution image. In consumer photography, super-resolution photographs are created using an overlapping panorama technique, which is combining multiple shifted images from the same camera. In multi-imager endoscope 15′, each of the image sensors 22 is directed generally distally towards the same object at a defined distance. Image sensors 22 may be mounted in the same flat plane and directed generally parallel to a center axis of the endoscope to provide images with some overlap. Alternatively, image sensors 22 may be directed convergently towards the object thereby increasing the amount of image overlap. As shown in FIG. 2, having the ultra-small image sensors 22 spread apart and mounted in an arrangement or array spanning the distal tip 23 of endoscope 15′ as far as possible can enhance the resolution of the computed output image. Computer 16 or 28 may use computational photography to create a super-resolution image that mimics an image from a hypothetical single higher resolution sensor that would span the most separated points of the sensor array, e.g. a single sensor spanning nearly the full diameter of insertion tube 20. Such a large single image sensor would have high resolution power, even greater power than the 160K pixels described above, but such a construction would not be practical because it would require the omission of other necessary or highly desirable endoscope features such as a light source and a working channel.

Additional potential software applications that may enhance or augment the images from multi-imager endoscope 15' include image magnification or conversion of two-dimensional images to three-dimensional images. Images may also be foveated, i.e. resolution is increased in one or more particular areas of interest in the image. Computer 16 may also identify critical structures, anatomies, cancerous tissue, high risk lesions, etc. to inform clinical decision making. As described in further detail below, three-dimensional positioning of the endoscope in space may be determined and displayed in the constructed image using electromagnetic navigation and/or inertial measurement units (IMUs) in the endoscope. Signals from multiple imagers 22 may also be used by computer 16 to affect/adjust handling characteristics of the endoscope or direct robotic guidance of the endoscope, as described in further detail below. The above capabilities may be created by using machine learning, artificial intelligence, and or computational photography.

To reconstruct an endoscope enhanced image, the images from each of the plurality of sensors need to be time-synchronized and co-registered. In consumer imaging, gaps between images received from adjacent sensors may be filled by inference or by interpolation, e.g. using bilinear interpolation, but the resulting images may not be sufficiently reliable for use in medical diagnosis or treatment because there is no actual image data from the gap areas. To construct an enhanced image suitable for a medical imaging device such as a multi-imager endoscope, the overlap of multiple images must be determined and leveraged. Computational algorithms that may be useful in multi-imager endoscopy include CLEAN (Högbom, J. A., Astronomy and Astrophysics Supplement, Vol. 15, p. 417) and regularized maximum-likelihood (RML) image restoration. Another image enhancement technique involves modulating the light source(s) on/off to provide different light angles for each sensor 22, thereby providing different information to computer 16 or 28. Typically, endoscope imagers are color sensors such as RGB sensors that detect red, green and blue colors. In an alternative embodiment of endoscope 15', one or more of the multiple color sensors may be replaced with an active or passive near-infrared sensor to provide additional diagnostic information such as temperature or proximity. A grayscale sensor may also be substituted in the imager array to add an increased sensitivity to the level of brightness as well as to be used in combination with selective wavelength illumination.

Ideal handling characteristics of an endoscope are dependent on the tortuosity of the anatomy. For ideal handling, the rigidity, flexibility and torsional requirements will be different for tighter anatomic turns from the requirements for milder anatomic turns. Computer 16 is configured for steering and/or adjusting torsional and bending stiffness characteristics of insertion tube 20 by driving the plurality of actuators 42 in response to a) one or more command inputs from the one or more haptic input devices 43, and/or b) data from distal IMU(s) 25 and intermediate IMU 27 identifying directional changes as insertion tube distal end 21 is pushed through the anatomy of the living body. Each discrete anatomic bend can be characterized by distal IMU(s) 25 and intermediate IMU 27 according to parameters such as bend length, angle of bend, and distance from prior bend. This data from distal IMU(s) 25 and intermediate IMU 27 can then be used by computer 16 to automatically and dynamically adjust bending stiffness and torsional characteristics to pre-defined specification ranges. During endoscopy, if distal IMU(s) 25 and/or intermediate IMU 27 do not register forward movement of insertion tube distal end 21 despite movement registered in proximal IMU(s) 44, then computer 16 may drive actuators 42 as necessary to adjust the bending stiffness and torsional characteristics of insertion tube 20 to facilitate forward movement of insertion tube distal end 21. Should forward movement of insertion tube distal end 21 be detected by distal IMU(s) 25 and intermediate IMU 27 in response to the adjustments, computer 16 will save data regarding the anatomical bend and bending stiffness/torsional characteristics in a memory function for future algorithm refinement.

Computer 16 is configured for creating a digital three-dimensional anatomy model by combining position and orientation data received from one or more IMUs 25, 27 and/or 44 and image data received from optical module 22. The image data received from optical module 22 comprises a plurality of image frames and the spatial pose data received from distal IMU 25 comprises discrete distal IMU pose data points, as measured by distal IMU 25 and/or intermediate IMU 27, sequentially arranged along a path traced through the living body by the insertion tube distal end 21. Computer 16 creates a digital three-dimensional or spatial image map for an anatomy model by associating each image frame or a sampling of image frames with a discrete distal IMU pose data point to create a discrete image pose datum. Each image pose datum is stored by computer 16 as a) a new reference and b) relative to prior references. As the path is re-traced through the living body by the insertion tube distal end, computer 16 replaces orientation data previously received from distal and proximal IMUs 25, 27 and/or 44 and replaces image data previously received from optical module 22. Computer 16 progressively stitches together each image frame or sampling of image frames from optical module 22 using the associated pose data point from distal IMU 25 to orientate the frames in a set of three-dimensional planes surrounding the path thereby creating a three-dimensional or spatial image map of the anatomy displayable as an endoluminal rendering on monitor 17. Since the rendered image derived from the three-dimensional or spatial image representation contains historical spatial data from distal IMUs 25 associated with each image frame and distal IMU 25 contains the current pose of insertion tube distal end 21 as well as information about the flexing tip of the endoscope, the current pose of insertion tube distal end 21 as well as the flexing tip can be referenced on the three-dimensional or spatial image model in real-time, thus enabling auxiliary portrayals of the anatomy to enable better understanding of the endoscope tip location and orientation. The overall path of the anatomy is discerned from the time series of the IMU poses with the image data surrounding these path points being available for display as needed to enhance understanding of anatomy being explored. Computer 16 can create an external representation of the approximate spatial path of the anatomy that can be shown simultaneously with video images from optical module 22.

If additional data regarding the measured distance from the distal end 21 to the anatomy surface is obtained, then computer 16 may portray the current location and orientation of insertion tube distal end 21 superimposed on an endoluminal rendering of the three-dimensional surface anatomy model on monitor 17. The distance from the distal end 21 to the anatomy surface may be measured by the multi-camera arrangement described above or by incorporating a structured-light three-dimensional scanner using projected light patterns, or a time-of-flight range-imaging camera (none of which are shown).

Computer 16 is also configured to provide the one or more manual rotary controls with kinesthetic or haptic communication relative to the tensile load applied by the one or more of the actuators to the corresponding cables. This haptic communication may be driven by computer 16 to emulate the manual feel of operating the steering wheels of a conventional, strictly mechanical endoscope. Emulation may be achieved by computer 16 by reference to a) calibration data for insertion tube 20, and/or b) pre-defined specifications, e.g. a series of pre-defined ratios of kinesthetic or haptic feedback to insertion tube kinematic outputs.

Calibration data may be associated with an individual insertion tube 20, as measured or determined during manufacturing, or calibration data may generally extend to a series or family of identical insertion tubes 20 along with their corresponding flexible tip sections 50. A memory module 45 containing calibration data may optionally be disposed within insertion tube 20, as shown in FIG. 1 as being located near the proximal end of insertion tube 20. For endoscopes 15 where handle 40 is releasably connected to insertion tube 20, computer 16 may set up specific emulation handling parameters based upon the calibration data read from memory module 45 in the connected insertion tube 20. Alternatively, the calibration data could be stored on board the insertion tube 20 as a quick response code (QR code) or similar barcode where the meaning of the code is either known to computer 16 or can be looked up via a network. In such an arrangement, handle 40 may include a suitable code reader adapted to view the QR code before, after, or during the connection of insertion tube 20 and handle 40, i.e. via connector 39.

As an example of a method of determining calibration data for an insertion tube 20, insertion tube 20 is manufactured and placed in a testing rig to determine how many rotations of a haptic rotary input device it takes to achieve flexion and torsion targets. These rotations are saved and stored on memory module 45 in insertion tube 20 and are used to calibrate the number of turns a haptic device 43 on the handpiece must turn in order to move insertion tube 20 to a consistent and predictable position. Thus, calibration data is indicative of the physical properties of an insertion tube 20. For example, if (input of) 2 turns in a manufacturing test rig are required to achieve a 180° bend (output) of insertion tube 20, but a pre-defined usage standard says a 180° bend should only require 1.5 turns, then the calibration data stored in memory module 45 will inform computer 16 to modify command inputs such that each turn of rotary input device 43 by a clinical user would actually make the associated actuator move 1.25 times (2/1.5).

Thus, computer 16 is configured to perform the following steps:

receive input commands from the one or more haptic rotary input devices 43, modify the input commands with reference to the calibration data readable in memory module 45, and use the modified input commands to drive the plurality of actuators and thereby operate the corresponding cables to consistently achieve a defined ratio of rotary control rotation inputs to insertion tube kinematic outputs.

In alternative embodiments, the haptic input devices may be other than rotary controllers. In such embodiments, the inputs would involve measures of motion in joysticks, movement of fingers on touchpads, or keyboard entries, etc. In one embodiment, computer 16 can drive the actuators to emulate a pre-defined manual sensation or feel of the device controls rather than, as in the above example, achieve an expected number of rotations to generate a certain bend in insertion tube 20. In this case, computer 16 uses the modified input commands to drive the plurality of actuators and thereby operate the corresponding cables to consistently achieve a defined ratio of kinesthetic haptic feedback to insertion tube kinematic outputs. With the above methods, a semi-robotic endoscope using the present technology can emulate the manual feel of a conventional strictly manual endoscope, thus requiring minimal training of a clinician accustomed to conventional devices.

Figures 12, 13, 14, 15:
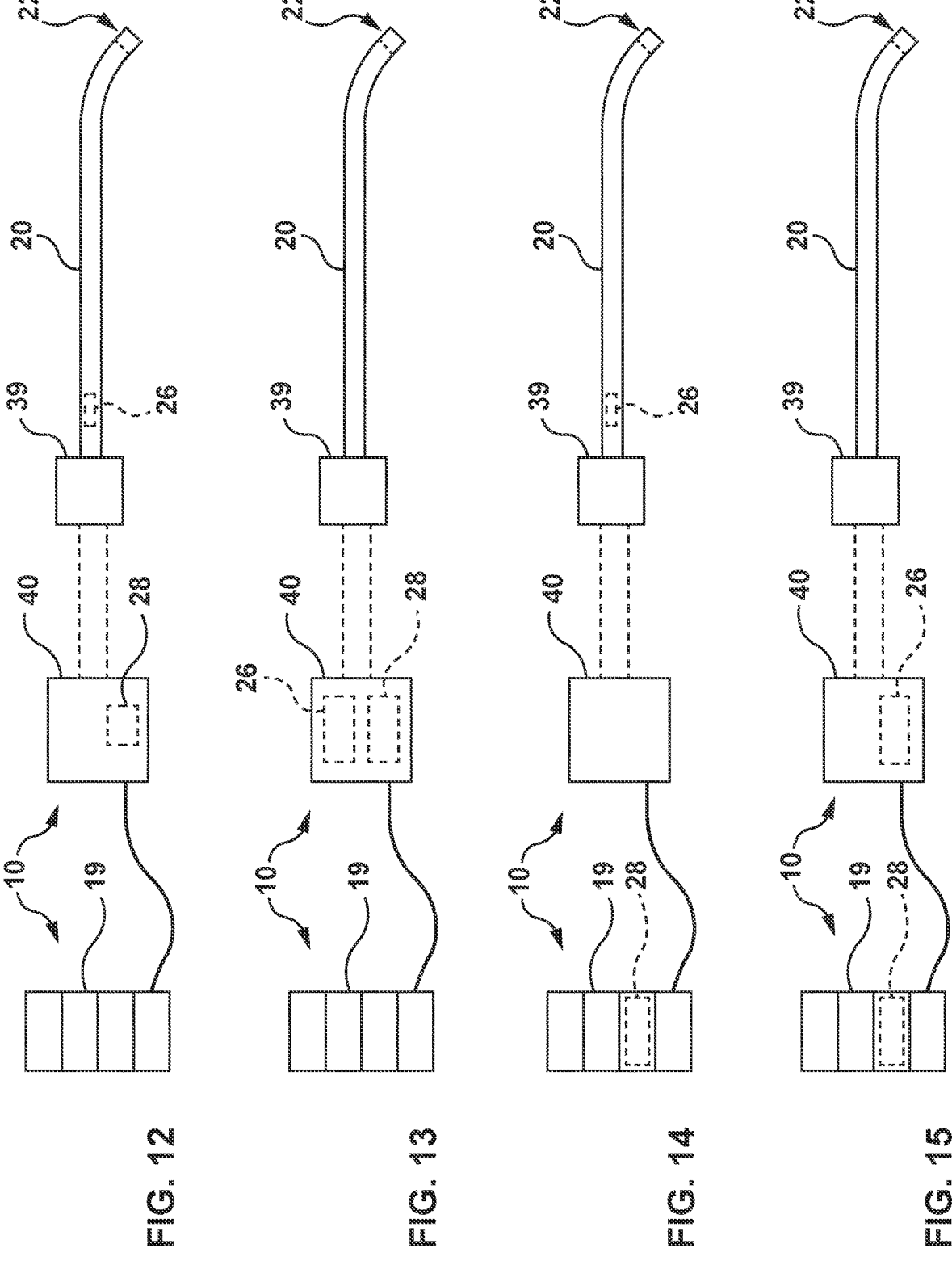
FIGS. 12-15 illustrate semi-schematically the locations of elements in various embodiments of the present technology.

During image-processing using multi-imager endoscope 15', image sensors 22 provide signals to image processor units (IPUs) 26. A computer circuit such as an application-specific integrated circuit (ASIC), or preferably a field programmable gate array (FPGA) 28 receives output signals from all IPUs 26. Alternatively, computer 16 can be configured to perform the multi-imager data processing function(s) ascribed herein to computer circuit 28. Thus, a multi-imager endoscope or endoscope system may comprise computer 16 or computer circuit 28 or both, wherein different functions are divided between the computers. Sensors 22 are located at the distal end of insertion tube 20, but IPUs 26 and FPGA 28 may be located in various places in endoscopy system 10, as illustrated semi-schematically in FIGS. 12-15. In FIG. 12, an IPU 26 is located in insertion tube 20; other IPUs 26 are omitted for clarity. FPGA 28 is located in removable handle 40. To facilitate data processing speed, it may be advantageous to mount IPUs 26 as close as possible to sensors 22 without diminishing the mechanical properties of insertion tube 20. In FIG. 13, IPU(s) 26 and FPGA 28 are located in handle 40. In FIG. 14, an IPU 26 is located in insertion tube 20; other IPUs 26 are omitted for clarity. FPGA 28 is located in endoscopy tower 19. In FIG. 15, IPU(s) 26 are located in handle 40 and FPGA 28 is located in endoscopy tower 19.

Figure 16:
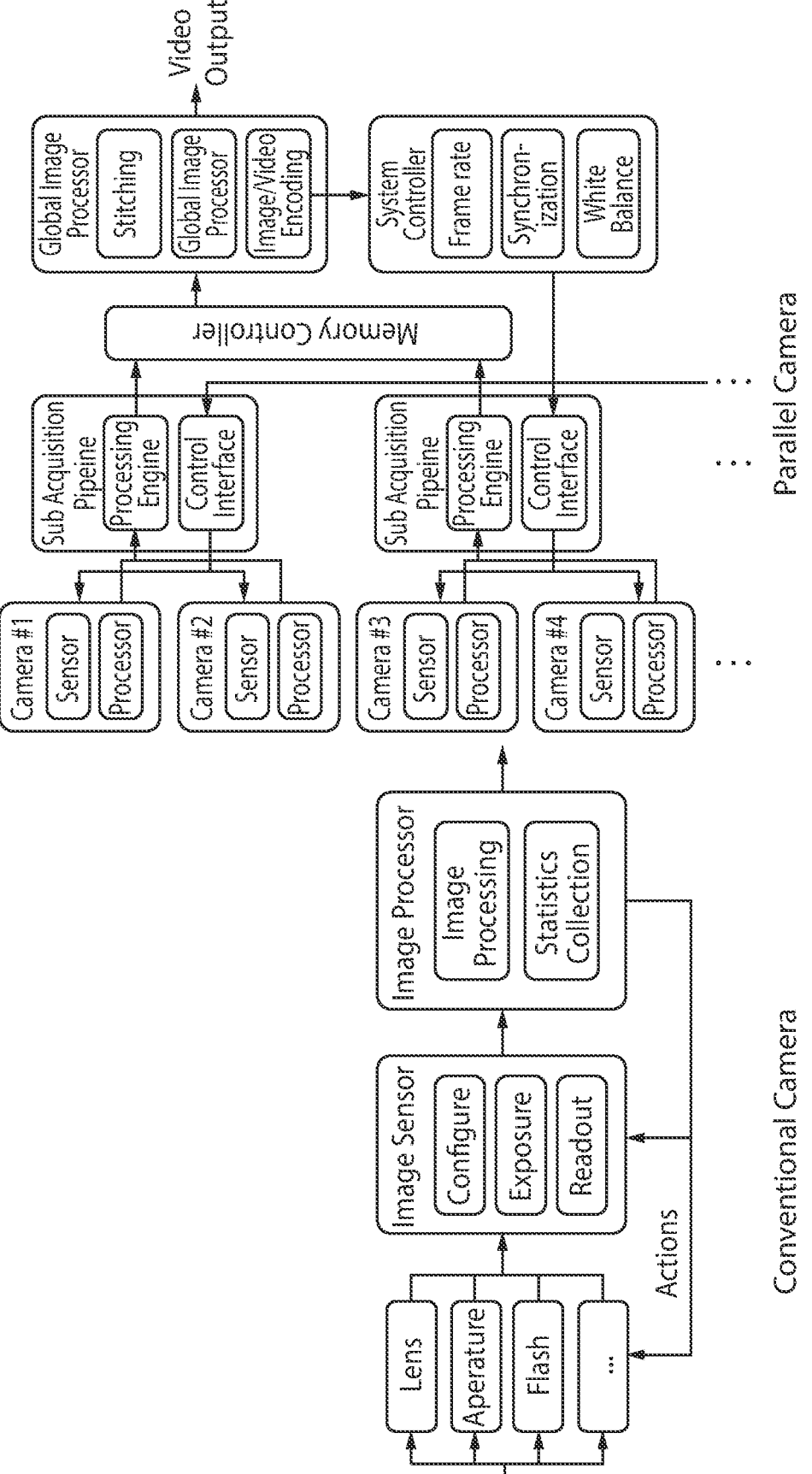
FIG. 16 schematically illustrates the difference between prior art signal processing systems for single-camera systems and multiple-camera systems.

Digital signal processing systems for multi-imager setups differ from single-camera systems such that parallel sensor and parallel image signal processing enable cost efficient and compact devices to capture gigapixel scale images, as illustrated schematically in FIG. 16.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. An endoscopy system comprising:
  an elongate insertion tube having a proximal end and a distal end, and an open working channel there through;
  two or more distally-facing image sensors mounted at the distal end of the elongate insertion tube, wherein each of the two or more distally-facing image sensors is operatively connected to a corresponding image processing unit (IPU) disposed in the elongate insertion tube;
  one or more inertial measurement units (IMUs) disposed on the elongate insertion tube, the one or more IMUs measuring IMU data comprising acceleration, angular rate, and magnetic field surrounding the elongate insertion tube;
  one or more light sources fitted at the distal end of the elongate insertion tube; and
  at least one computer processor operatively connected to each of the IPUs disposed in the elongate insertion tube, the at least one computer processor being configured for applying computational photography to data received from each of the IPUs disposed in the elongate insertion tube to create an enhanced output image, and further configured for associating the data received from each of the IPUs with the IMU data to remove navigation errors of the elongate insertion tube and create an image pose datum.

2. The endoscopy system of claim 1, wherein the enhanced output image is a result of one or more computational photography techniques selected from super-resolution, foveation, magnification, and two-dimensional to three-dimensional conversion.

3. The endoscopy system of claim 1, wherein the at least one computer processor is selected from an application-specific integrated circuit (ASIC) or a field programmable gate array (FPGA), and is disposed in a handle connected to the proximal end of the elongate insertion tube or in an endoscopy tower.

4. The endoscopy system of claim 1, wherein the at least one computer processor comprises a computer circuit dedicated to performing the computational photography and a computer dedicated to performing functions other than the computational photography.

5. The endoscopy system of claim 1, wherein the at least one computer processor is configured for applying the computational photography using an image processing algorithm selected from CLEAN and regularized maximum-likelihood (RML) image restoration.

6. The endoscopy system of claim 1, wherein the two or more distally-facing image sensors comprise a same type or different types of image sensors selected from color sensors, infrared sensors and grayscale sensors.

7. The endoscopy system of claim 1, wherein the one or more light sources comprise a same type or different types of light sources selected from distally-mounted light-emitting diodes (LEDs) or fiber optic light guides.

8. The endoscopy system of claim 1, wherein the two or more distally-facing image sensors consist of four ultra-small $200 \times 200$ pixel image sensors measuring $0.575$ mm$\times 0.575$ mm, the open working channel has a diameter of $2.1$ mm, and the elongate insertion tube has an outer diameter of $3.25$ mm.

9. The endoscopy system of claim 1, further comprising a computer circuit disposed in a handle connected to the proximal end of the elongate insertion tube, the computer circuit being operatively connected to each of the IPUs in the endoscopy system and being configured for applying the computational photography to the data received from each of the IPUs disposed in the elongate insertion tube to create the enhanced output image.

10. The endoscopy system of claim 1, wherein the one or more IMUs provide pitch, roll, and yaw as well as linear movement.

11. The endoscopy system of claim 1, wherein the IMU data is utilized to calculate attitude, angular rates, linear velocity and position relative to a global reference frame.

12. The endoscopy system of claim 1, wherein the at least one computer processor is configured to create a digital three-dimensional or spatial image map for an anatomy model by associating a sampling of image frames with a discrete IMU pose data point to create a discrete image pose datum.

13. The endoscopy system of claim 12, wherein the at least one computer processor is configured to progressively stitch together the sampling of image frames using an associated discrete IMU pose data point to orient the sampling of image frames in a set of three-dimensional planes surrounding a path, thereby creating the digital three-dimensional or spatial image map for the anatomy model.

* * * * *